United States Patent [19]

Pungor et al.

[11] Patent Number: 4,673,295
[45] Date of Patent: Jun. 16, 1987

[54] METHOD AND AN APPARATUS FOR PERFORMING ROUTINE ANALYSES SUCH AS POLAROGRAPHIC OR SPECTROPHOTOMETRIC ANALYSIS

[75] Inventors: Erno Pungor; Klára S. Tóth; Zsófia Fehér; Géza Nagy; György Horvai, all of Budapest, Hungary

[73] Assignees: Richter Gedeon Vegyészeti Gyár; Budapesti Müszaki Egyetem, both of Budapest, Hungary

[21] Appl. No.: 850,431

[22] PCT Filed: Jun. 17, 1983

[86] PCT No.: PCT/HU83/00034
§ 371 Date: Feb. 1, 1984
§ 102(e) Date: Feb. 1, 1984

[87] PCT Pub. No.: WO84/00065
PCT Pub. Date: Jan. 5, 1984

Related U.S. Application Data

[63] Continuation of Ser. No. 584,439, Feb. 1, 1984, abandoned.

[30] Foreign Application Priority Data

Jun. 18, 1982 [HU] Hungary .............................. 1986/82

[51] Int. Cl.$^4$ .............................................. G01N 21/00
[52] U.S. Cl. ...................................... 356/440; 356/246
[58] Field of Search ............................... 356/440, 246

[56] References Cited

U.S. PATENT DOCUMENTS

| | | | |
|---|---|---|---|
| Re. 30,391 | 9/1980 | Liston ................................ | 356/246 |
| 3,501,064 | 3/1970 | Gaumer .............................. | 222/571 |
| 3,869,214 | 3/1975 | Egli et al. ........................... | 356/246 |

Primary Examiner—Bernard D. Pianalto
Attorney, Agent, or Firm—Gabriel P. Katona

[57] ABSTRACT

In a method and an apparatus for performing routine analyses such as polarographic or spectrophotometric analysis on a large set of sample solutions filled into separate sample cups being arranged on or shaped in a sample cup holder (101) along a moving path, wherein the samples are in consecutive cycles sucked out of the sample cup (102) by a suction tube (103) and transferred into a common vessel, wherein the analysis will be performed. The vessel (105) has a lower outlet (107) communicating with an analyzer cell (112) or the ambient space over a channel (116) which is only effective if the sample level in the vessel (105) exceeds a certain threshold level, and an aspirating mouth (108) in the upper part of the vessel (105) communicating over a valve (109) with the ambient space. The suction tube (103) has a fixed end coupled to the inlet (106) of the vessel (105) and a free end can be moved into two different working positions. A continuous suction effect is exerted on the fixed end of the suction tube during the whole series of cycles whereas the free end of the suction tube is in the first phase of each cycle moved into its first working position wherein the free end is dipping into the next sample cup and being thus positioned opposite to the suction tube and in the second phase turned into its second working position wherein the free end is protruding into the ambient space. The analysis is performed when the level of the sample in the vessel has already exceeded a prescribed threshold level and at the end of the analysis operation an overpressure is established in the vessel. Then the suction tube, as the phase of the next following cycle, is moved again into its first working position and this series of operations is cyclically repeated.

2 Claims, 3 Drawing Figures

METHOD AND AN APPARATUS FOR PERFORMING ROUTINE ANALYSES SUCH AS POLAROGRAPHIC OR SPECTROPHOTOMETRIC ANALYSIS

This is a continuing application of application Ser. No. 584,439, filed on Feb. 1, 1984, now abandoned.

TECHNICAL FIELD

The invention relates to a method and an apparatus which make routine serial analysis of a large number of solution samples possible in a manner that the transfer of the samples from the sample cups into the vessel wherein the analysis is performed may in certain cases be carried out—with sufficient precision—more easily than according to prior art. The invention is especially advantageous in case of polarographic or spectrophotometric analyses so that it will hereinafter particularly be set forth with reference to such examples but it will be apparent to persons ordinarily skilled in the art that the advantages of the invention may also be obtained in the course of other types of analyses provided that the conditions are similar ones.

The invention provides a novel way for handling the samples in a universal manner so that it may be used with routine analyses where the handling in itself shall be solved as well as with routine analyses where the handling should preferably be combined with a certain pre-treatment of the sample such as the deoxygenation (hereinafter: deaeration) as necessary before performing the polarographic analyses.

It can be seen from the following that the invention comprises main features common to all analyses it may be applied with whereas additional features will be apparent characteristic for the very type of analysis shown in any of the following examples. The spectrophotometric analysis e.g. is according to the invention carried out by handling the samples in a manner which may also be applied with fluorescence measurements whereas the combined handling and pre-treatment as performed in the course of the polarographic analysis can also be applied using working electrodes other than the dropping mercury electrode, i.e. with different types of voltametric methods.

The extent of automation can also be greatly varied: on the one hand the mechanisation of sample introduction and emptying is a crucial starting point for the automation of which may be sufficient in itself, but on the other hand, the whole process, i.e. all steps of the analyzing procedure can be automated altogether and that either using a built-in microprocessor or processing it from an external automatic system.

BACKGROUND ART

The sample handling apparatuses according to prior art can be classified according to a main feature:

One group comprises the apparatuses for analyses wherein each sample is analyzed in a different vessel, the other group comprises the apparatuses wherein the cyclically changed samples are analyzed in one and the same vessel (e.g. a section of the tube) either after only removing the previously analyzed sample or after cleaning the vessel following the removing of the previous sample.

The first group is disadvantageous in so far that each vessel shall either be thrown away or picked out of the analyzer channel, specially cleaned and again incorporated into the analyzer channel. The process is also more complicated because the analyzing means such as the electrode used for the polarographic analysis shall be moved from the one vessel into the other one and also the electrodes shall be cleaned after each cycle. The PARC Model 316 Automatic Cell Sequencer (Princeton Applied Research; PAR) belongs to this group.

The other group is disadvantageous in so far that it can not generally be used, e.g. samples for polarographic analysis can not be handled by such apparatuses. The Auto Analyzer (manufactured by Technicon Corp.) belongs to this group.

DISCLOSURE OF THE INVENTION

The invention is based on the concept that the sample handling can in any case uniformly be automatized in a manner that also the pre-treatment, if necessary, can be included into the automatized process if the samples are transferred from the sample holding cups (hereinafter: sample cups) into a properly designed common vessel wherein the analysis (or its first step) can be performed in a manner that the transferring process consists of two phases, a vessel is used communicating with the ambient space over two channels providing different communication conditions, a suction tube is used one end of which (hereinafter: fixed end) can be attached—intermediately or by way of a pump—with the inlet of the vessel whereas the other end (hereinafter: free end) is arranged in a manner that it can be turned into two different working positions, in the first working position it is dipped into the sample cup having its turn and being moved opposite to the suction tube and, in the second position, it is protruding into the ambient air, a continuous suction is exerted during the whole cycle series on the fixed end of the suction tube but the free end of the suction tube is during the first phase of each cycle turned into the first working position (i.e. dipped into the sample cup) whereas the free end is during the second phase of each cycle turned into the second working position (i.e. protruding into the ambient air).

A preferred embodiment of the invention is differing from the above only in so far that the communication conditions of one of the channels between the vessel and the ambient space are in the second phase of each cycle also amended e.g. the said channel is in the first phase open and in the second phase closed. This way, it can be ensured that the vessel in which the analysis or its first step is carried out is cyclically emptied by way of flushing it with air or a suitable other gas. The sample is introduced into the vessel containing at that time only air or the said other gas, the level of the sample in the vessel is thereby continuously increasing notwithstanding the fact that at the same time a portion of the input sample is leaving the vessel over its outlet. Thus, the sample level in the vessel will after once exceeding a certain threshold level, for a certain period of time not sink below the said threshold level, this period to be chosen long enough for accomplishing the analysis procedure.

The analysis can thus be performed on a resting sample (in case of the polarographic analysis) or a quasi-resting sample (in case of the spectrophotometric analysis) which offers more reliable conditions for a precision measurement. A resting state of the sample could according to prior art only be obtained by interrupting the suction applied on the suction tube. The process according to the invention provides, however, a (virtual) rest of the sample in the vessel offering just similar measuring conditions without the need of interrupting the suction effect on the suction tube. During the measuring period, the suction causes an air-flow (gas flow) over the upper outlet of the vessel whereas the lower outlet is either closed (in case of polarographic measurement) or letting out such small a portion of the sample that the sample level in the vessel does not sink below the threshold level (in case of spectrophotometric measurement) so that it is a common feature of all types of measuring that the suction effect is not interrupted, the filling and emptying phases are melting into each other in a manner that no separating dead times are necessary, and the (quasi-)continuous delivery of the sample solution can be performed using a minimum of means.

According to prior art, the deaeration was generally performed in the cell wherein also the analysis was performed. It is a special advantage of the method according to the invention that the pre-treatment and the analysis can be performed in different areas separated from each other.

The sample from the sample cup is sucked into the pre-treatment stage, i.e. a deaeration vessel preceding the analysis cell. After the deaeration is performed, the sample is by causing a gas overpressure transferred into the analysis cell. Since the sample pre-treatment and the analytical process is separated in space, the two steps can be performed parallely and, thus, the rate of the polarographic analysis is increased appreciably.

Accordingly, the advantages of the invention against prior art can be summarized as follows:

versatility; it can be in combination used with other detection systems, too;

uniform sample handling including continuous sample introduction, emptying and drying out of the vessel before filling in the next sample. The sample handling is uniform independently of whether the whole analysis procedure is carried out in the same vessel or the sample will proceed to a further analysis cell. The universal sample handling process comprises only two—filling and emptying—phases in a cycle. Auxiliary steps such as pre-treatment can easily be incorporated into the process without the need of amending the handling operations and, accordingly easily be fitted to the automation of the whole analytical procedure.

The subject matter of the invention thus comprises, on the one hand a method for performing the analysis of a large set of sample solutions—preferably their polarographic or spectrophotometric analysis—in the course of which the single samples to be analyzed are in consecutive cycles sucked out of the sample cup and transferred into a common vessel wherein the analysis (or its first step) will be performed. The improvement consists in that (a) a vessel is used having besides an inlet on the one hand, a lower outlet of which is communicating with a further receptacle such as analyser cell, or the ambient space over a channel which is only effective if the sample level in the vessel is exceeding a certain threshold level and on the other hand an aspirating mouth in the upper part of the vessel communicating over a valve (hereinafter: flushing valve) with the ambient space, (b) a suction tube is used one end of which (hereinafter: fixed end) can be coupled to the inlet of the vessel or a channel communicating with the said inlet whereas the other end (hereinafter: free end) of the suction tube can be turned into two different working positions, (c) the fixed end of the suction tube is coupled to the said inlet or the said channel, (d) a continuous suction effect is exerted on the fixed end of the suction tube during the whole series of cycles whereas (e) the free end of the suction tube is in the first phase of each cycle turned into its first working position wherein the free end is dipping into the sample cup having its turn and being, thus, positioned opposite to the suction tube and in the second phase turned into its second working position wherein the said free end is protruding into the ambient space, and (f) the (first step of the) analysis is performed when the level of the sample in the vessel has already exceeded a prescribed threshold level and at the end of the (first step of the) analysis operation an overpressure is established in the vessel, and (g) then the suction tube is—as the first phase of the following handling cycle—again turned into its first working position and this series of operations is cyclically repeated.

In a preferred embodiment a vessel is used the upper and lower outlet of which being—over separate suction tubes of a pump (system—in communication with the following spaces of the analyzer chain e.g. the upper outlet with the ambient space and the lower outlet—preferably over the ambient space—with the waste; a continuous suction effect is exerted on both outlets of the vessel during the whole series of cycles, and the analysis is performed when the level of the sample in the vessel has already exceeded a prescribed threshold level.

Another object of the invention consists in an apparatus for performing routine analyses preferably spectrophotometric or polarographic analysis on a large set of sample solutions comprising the usual components necessary to perform the intended analyses and a set of individual sample cups arranged on or shaped in a sample cup holder such as a rotatable tablet along a moving path and a suction means arranged between the sample cup and a vessel wherein the (first step of the) analysis can be performed wherein the improvement consists in that the suction means is a suction tube one end (the fixed end) of which being—preferably over a dissolvable means—connected to the suction side of a fluid transporting device being in a communication with the inlet of the said vessel, and the support of the suction tube is comprising a means for turning the other end (free end) of the suction tube into two different working positions, and the outlet of the vessel is communicating with a further receptacle such as analyzer cell or the ambient space over a channel which is only effective if the sample level in the vessel is exceeding a certain threshold level, and an aspirating mouth is formed in the upper part of the vessel communicating over a valve with the ambient space.

In a preferred embodiment the fixed end of the suction tube is connected to the inlet of the vessel and the upper and lower outlets of the vessel are over different suction channels of a pump (system) communicating with spaces following the vessel, e.g. the upper outlet with the ambient space and the lower outlet—preferably over the ambient space—with a waste.

Preferably the suction tube is provided with an automatic means for changing the working positions, and the actuating device(s) of the pump (system) and the means for changing the working positions of the suction tube are provided with a connecting device fitted to the interface of a processor.

The apparatus according to the invention may comprise a built-in processor such as microprocessor.

The spectrophotometric analysis can be performed in a cuvette shaped in the conventional (square) form but in a manner that both its filling and emptying may be performed without the need of valves or other mechanical barring means. It is also an advantage, that the de-aeration needed as a pre-treatment in polarographic analysis is carried out automatically, but under the same circumstances as with the conventional manual polarographic analysis, thus, the efficiency of the process is the same as according to the prior art. The system becomes, thus, a very flexible one e.g. and widely used polarographic technique can thus be performed. The current measurement can be performed in one cycle not only at constant working electrode potential—which has to be selected in advance—but a whole polarogram (electrode potential-current curve) can be taken for each sample solution. Since the sampling, the deaeration and polarographic analysis are performed in phases following each other without separating dead times, the number of realizable cycles (number of samples that can be analysed) in a time unit is relatively large; during the analysis of the sample deaerated in the previous cycle, the deaeration of the next sample can already be performed.

THE BRIEF DESCRIPTION OF THE DRAWINGS

The invention will now be discussed more particularly with reference to the attached drawings.

BEST MODES FOR CARRYING OUT THE INVENTION

Figure 1:
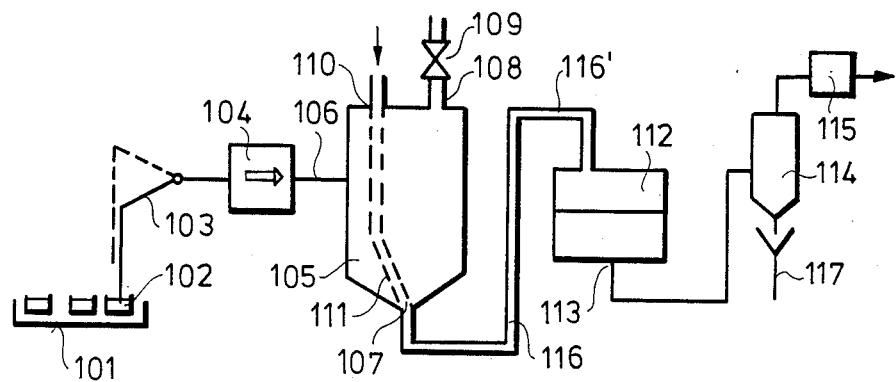
FIG. 1 is showing the block diagram of a preferred embodiment of the apparatus according to the invention.

It can be seen in FIG. 1 that a suction tube (hereinafter: probe) 103 is arranged between on the one hand the vessel 105 and on the other hand the tablet 101 carrying the sample cups in a manner that the said probe 103 may be transferred from its first working position to its second one and vice versa. One (the fixed) end of the said probe 103 is connected to said vessel 105 during the whole analytical procedure, while the other (the free) end of it is in the first working position dipped into the sample solution having its turn and being positioned opposite to said probe 103 and in the second working position the free end is in communication with the ambient space (dotted line).

The pump 104 is exerting a suction effect on the fixed end of the probe 103 and thus delivering to the inlet 106 of the vessel 105 in the first working position sample solution and in the second working position air. At the beginning of the first phase of a cycle, the vessel 105 is containing only air, the valve 109 is open, and an occasionally used pump 115 is at stillstand. A gas of appropriate composition (e.g. $N_2$; $H_2$; $Ar_2$) is in the course of the whole measuring procedure through a gas inlet tube 110 continuously introduced into the said vessel 105 at a roughly constant rate. The tube 116 may be designed in the manner as shown in FIG. 1 but it may also be inside the vessel 105. In both cases it will prevent the sample solution arriving into the vessel 105 to be transferred to the following receptacle such as analyzer cell 112 until the level of the sample solution inside the vessel 105 will not exceed the level of the highest section 116' of the tube 116. The tube 116 is thus a channel which is only effective if the sample level in the vessel 105 is exceeding a certain threshold level. The level in the said vessel 105 is rising during the first phase of the cycle. To avoid the over-fill, the operation of the said probe 103 is controlled in a manner, that the volume of the sample solution transferred into said vessel 105 during the whole period of the first phase sucked corresponds to a threshold level being the highest allowed level of the sample in the said vessel 105. After suction of this volume said probe 103 is lifted out from the sample cup and the suction leads to the transfer of ambient air into the vessel 105. The air delivered by the probe 103—through the pump 104 and the inlet 106—enters the vessel 105 wherefrom it leaves through on the one hand the aspirating mouth 108 and on the other hand the valve 109.

As a consequence of this working mode, the vessel 105 will after the first phase be filled with the first sample up to the highest level. The analytical measurement or pre-treatment in the said vessel 105 can, however, be started at any time during the filling and it can be sustained for any time after the entry of the total sample volume, since the delivery of air does not diminish the sample volume until the valve 109 remains open.

The vessel 105 can be a spectrophotometric cuvette which is illuminated through the two windows arranged on the two opposite sides of the vessel at an appropriate height, so that the measurement can be performed when the sample level has reached the upper level of the windows. It can also serve as a deoxygenating vessel into which an inert gas is continuously introduced.

After finishing the pre-treatment or the measurement in the said vessel 105, valve 109 will be closed. The air (and gas) can not leave through the valve 109 any longer so that an overpressure arises causing the transfer of the sample from the said vessel 105 into the further receptacle (analyzer cell) 112.

After this step, valve 109 will be opened again. Meanwhile, said probe 103 is again dipping now into the second sample and the second sample can enter the vessel 105 through said inlet 106. At this time starts the filling of the vessel 105 with the second sample. The whole process is now repeated and this occurs in each cycle.

It can be seen that the measurement in the cell 112 can be performed at the same time when the pre-treatment of the next sample is running. If the cell 112 is used for analytical measurement, thus the emptying of this cell 112 is ensured before the entrance of the second sample into said cell 112. For this reason the pump 115 is activated after finishing the measurement in cell 112 and thus the pump sucks the content of said cell 112 into the vessel 114 through tube 113. The operation of the pump 115 is stopped before the valve 109 is closed again. Thus, the first sample is transferred from vessel 114 to waste 117. If the measurement is performed in the vessel 105 itself, then the use of components 112-115 is superfluous and instead of cell 112 there is used the waste.

Figure 2:
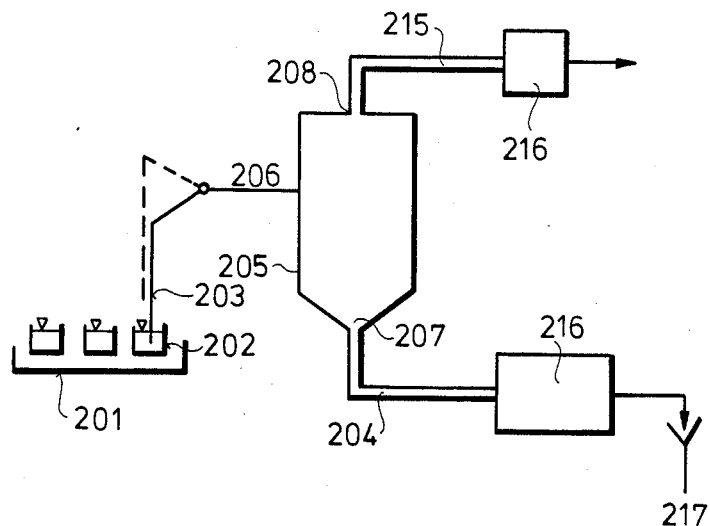
FIG. 2 shows another preferred embodiment which can be used for spectrophotometric analyses.

In certain cases it is not advisable to transfer the sample solution through the pump because the materials of the pump interacting with the samples can cause undesirable changes in the sample solutions. In this case the reverse of the order of the pump 104 and vessel 105 is expedient (FIG. 2). This means, however, that pump 104 has to be connected to the outlet tube 116 of the vessel 105, and this does not make possible the cyclic filling and emptying of the vessel 105. Because of this, pump 115 is connected to the aspiration tube 108 of vessel 105 instead of valve 109. The suction rates of pumps 104 and 115 are adjusted in an appropriate manner e.g. one to one. In this case both pumps work continuously. The procedure of the analysis is the following (FIG. 2):

The probe 203 depending on its working position sucks either sample or air. At the beginning of the procedure, the vessel 205 is empty. The speed of suction through the probe 203 is the sum of the suction speeds in channels 204 and 215, respectively. As the sample reaches the inlet slot 206 it flows down to the bottom of the vessel. From here a portion of the sample is sucked by the pump 216 through the lower outlet tube 204 but the level of the liquid will rise according to the suction speed in channel 215. The probe 203 is dipping into the sample for a time interval which is sufficient to achieve a threshold level in vessel 205. After exceeding the threshold level, the probe 203 will lift out of the sample.

When the air sucked by probe 203 has achieved the inlet 206 of the vessel 205 the emptying of vessel 205 starts because in this case the pump 215 through the outlet tube 204, the vessel 205 and probe 203 is in communication with the ambient space. The speed of emptying is equal to the solution speed in channel 204. The timing of dipping the probe 203 into the second sample is so that the second sample will reach the inlet 206 of vessel 205 when emptying of vessel 205 is complete.

With this arrangement in vessel 205 only the measurement can be performed e.g. spectrophotometric measurement. The measurement is performed during that time interval when the level of the solution is higher than the threshold level.

Figure 3:
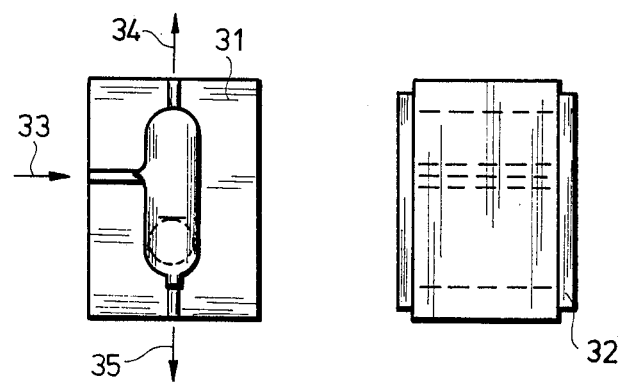
FIG. 3 shows a sketch of a cuvette that can be used in the apparatus as shown in FIG. 2.

In FIG. 3 a preferred embodiment of the analyzer cell suitable for spectrophotometric analysis is shown. The material of the cell body can be e.g. plexiglass, the light transmitting window of it can be of glass or quartz. The size of the cuvette as well as the flow rate has to be selected in accordance with each other and with the conditions of the measuring procedure.

Persons ordinarily skilled in the art can—if already knowing the above—design the whole automatic apparatus using components and units belonging as such to prior art.

The functional chain shown in FIG. 1 and FIG. 2 can be adopted for other analytical measurements, too. A cuvette can be embodied not only for spectrophotometric measurement but also e.g. for fluorescence measurement. A number of other variations can also be possible with keeping the main features of the procedure. The material of vessels and channels, as well as the type of valves, pumps, etc. can also be varied.

Obviously the different parts of the system can be controlled manually but the whole procedure can be automatized and there can be used different units for the data collection and handling. The process and the apparatus according to the invention can be useful for process control, too, if sampling and analysis is performed time to time at certain point of a technological process.

We claim:

1. A method for performing polarographic analysis on a large set of sample solutions filled each into a separate sample cup, said sample cups being arranged on or formed in a sample cup holder such as a rotatable tablet, in the course of which the single samples to be analyzed in consecutive cycles are sucked out of the sample cup and transferred into a common vessel wherein removal of oxygen is performed, comprising the (a) employing a vessel having an inlet and a lower outlet, an aspirating mouth and gas introductive means, communicating said vessel with a further receptacle such as analyzer cell or the ambent space over a conduit only if the sample level in the vessel is exceeding certain threshold level and below said threshold level communicating said vessel over said aspirating mouth in the upper part of the vessel communicating over a valve with the ambient space, said gas introducing means comprising a tube protruding into the vessel toward a bottom portion thereof and through which a gaseous medium is supplied continuously during all succeeding cycles of the analysis, (b) employing a suction tube and coupling a fixed one end thereof to the inlet of the vessel, a free end of the suction tube being movable into two different working positions, (c) a continuous suction effect is exerted on the fixed end of the suction tube during series of cycles, whereby said suction tube depending on its working position sucks up either the sample or ambient air, thereby a virtual restposition is created for said sample in said analyzer cell for performing the analysis, (d) the free end of the suction tube in the first phase of the next cycle is moved into a first working position wherein the free end is dipping into the next sample cup positioned opposite to the suction tube after emptying said vessel, and in the second phase moved into a second working position wherein said free end is protruding into the ambient space, and (e) performing at least the first step of the analysis after the level of the sample in the vessel exceeded a prescribed threshold level and, at the end of the first step of the analysis after completing said removal of the oxygen by said introduction of said gaseous medium an overpressure is established in the vessel, by closing said valve and communicating said aspirating mouth with the ambient space, whereby said sample is moved from said vessel into said polarographic cell, (f) moving the suction tube during the first phase of the following handling cycle into its first working position and repeating this series of operations cyclically.

2. An apparatus for performing routine analysis preferably spectrophotometric or polargraphic analysis on a large set of sample solutions comprising an analysis vessel, a set of individual sample cups arranged on a sample cup holder along a moving path, a suction means arranged between the sample cup and said vessel wherein at least the first step of the analysis is to be performed, said suction means is a suction tube comprising means for turning an other end of the suction tube into two different working positions, and the outlet is communication with further receptacle comprising an analyzer cell over a conduit effective if the sample level in the vessel is exceeding a certain threshold level, and an aspirating mouth formed in the upper part of the vessel communicating over a valve with the ambient space, a gas introducing means comprising a tube protruding into the vessel toward a bottom portion thereof and through which a gaseous medium is supplied continuously during all succeeding cycles of the analysis, means for exerting a continous suction effect on the suction tube whereby said suction tube depending on the working position thereby sucks up either the sample or ambient air, thereby a virtual restposition is created for said sample in said analyzer cell for performing the analysis and after completing said removal of the oxygen by said introduction of said gaseous medium an overpressure is established in the vessel by closing said valve and communicating said aspirating mouth with the ambient space, whereby said sample is moved from said vessel into said polarographic cell, means for moving said suction tube into a first working position of a next cycle for dipping into the next sample after said vessel is empty of the first sample.

* * * * *